United States Patent [19]

Hirose et al.

[11] Patent Number: 5,362,635
[45] Date of Patent: Nov. 8, 1994

[54] PROCESS FOR THE PRODUCTION OF AN AMINO ACID USING A FERMENTATION APPARATUS

[75] Inventors: Toshiki Hirose; Minoru Tsuruta, both of Kawasaki; Koji Tamura, Saga; Yoshitomo Uehara; Harufumi Miwa, both of Kawasaki, all of Japan

[73] Assignee: Ajinomoto Co., Inc., Tokyo, Japan

[21] Appl. No.: 82,459

[22] Filed: Jun. 25, 1993

Related U.S. Application Data

[62] Division of Ser. No. 764,210, Sep. 23, 1991, Pat. No. 5,260,216.

[30] Foreign Application Priority Data

Sep. 21, 1990 [JP] Japan .................................. 2-49983

[51] Int. Cl.$^5$ ..................... C12P 13/04; C12P 13/14; C12P 7/14; C12P 1/04
[52] U.S. Cl. ..................... 435/106; 435/110; 435/162; 435/170; 435/246; 435/284; 435/287; 435/311; 435/313; 435/315; 435/316; 435/812; 435/813; 435/819
[58] Field of Search ............... 435/106–110, 435/162, 170, 246, 812, 813, 284–287, 311, 313, 316, 315, 819

[56] References Cited

U.S. PATENT DOCUMENTS 3,002,889  10/1961  Kinoshita et al. ............... 195/47
3,096,252  7/1963   Motozaki et al. ................ 195/47

FOREIGN PATENT DOCUMENTS 2048394  3/1987  Japan .

OTHER PUBLICATIONS

Japanese Laid-open Application 48394/87 Abstract, Mar. 1987.

Primary Examiner—Douglas W. Robinson
Assistant Examiner—Deborah K. Ware
Attorney, Agent, or Firm—Maier & Neustadt Oblon, McClelland

[57] ABSTRACT

Amino acid fermentation is conducted by fermenting bacterial cells in a culture medium in a fermentor and separating fermentation solution withdrawn from the fermentor into a solution containing said bacterial cells and a solution not containing bacterial cells by a cell separator. The solution containing said bacterial cells being circulated from said cell separator to said fermenter by circulating means to perform amino acid fermentation continuously, and bubbles being removed from said fermentation solution by a bubble separator before said fermentation solution is fed to said circulating means and said cell separator.

4 Claims, 2 Drawing Sheets

PROCESS FOR THE PRODUCTION OF AN AMINO ACID USING A FERMENTATION APPARATUS

This is a division of application Ser. No. 07/764,210, filed on Sep. 23, 1991 now U.S. Pat. No. 5,260,216.

BACKGROUND OF THE INVENTION

1. Field of the Invention

The present invention relates to a process and an apparatus for amino acid fermentation employing bacterial cells in which the fermentation solution containing bacterial cells is recirculated for use in continuous amino acid fermentation.

2. Description of the Background

Methods, such as the additional feeding of sugar or the like and the supply of sufficient oxygen, as demanded by bacterial cells, have been proposed for improving the fermentative production of an amino acid such as glutamic acid. None of these methods, however, have resulted in any greatly increased production of amino acids, since a decrease of cell density and a lowering in the capacity for amino acid production occurs during the latter part of the fermentation process.

A process has been proposed which is a continuous culturing process in which basically a portion of the fermentation solution is withdrawn from a fermenter, the withdrawn solution is then separated into a solution containing bacterial cells and a solution which does not contain bacterial cells in a cell separator, and the former solution is recycled to the fermenter (Japanese Patent Application Laid-Open No. 48394/1987). The continuous culturing process has exhibited a very high level of productivity during its experimental stage in comparison to other known processes. However, it has been more difficult to carry out this process successfully on a large scale, in comparison to experimental size operations which are carried out on a smaller scale and which do not present any significant problem.

The known continuous culture process essentially calls for circulation of the fermentation solution from a fermenter to a cell separator and from the cell separator to the fermenter. Obviously, various kinds of pumps must be used to achieve this circulation. One of the pumps is a tube pump. However, no satisfactory tube pump has been available which can smoothly circulate a large amount of the fermentation solution when the process is carried out on a large commercial scale, even though a tube pump exists which is useful when the process is carried out on a small experimental scale.

Amino acid fermentation, such as glutamic acid or lysine fermentation, is aerobic fermentation which calls for aeration and agitation, and yields a fermentation solution containing a large amount of bubbles. These bubbles cause cavitation in any pump which is used other than the tube pump and prevent the smooth circulation of the fermentation solution. Accordingly, it has hitherto been impossible to carry out the continuous culturing process successfully on a commercial basis, because there has not been any alternative but to use a pump which is other than a tube pump, and therefore the problem of cavitation by bubbles is encountered.

The bubbles create a great resistance to the circulation of the solution in a pipeline, and also lower the performance of the cell separator if it is of the centrifugal type. Accordingly, a need continues to exist for an improved continuous process for amino acid fermentation.

SUMMARY OF THE INVENTION

Accordingly, one object of the present invention to provide a process and an apparatus which enable continuous culturing for amino acid production to be carried out on a large scale.

Briefly, this object and other objects of the present invention as hereinafter will become more readily apparent can be attained in a process for amino acid fermentation by the fermentation of at least bacterial cells in a culture medium in a fermenter, and a cell separating step for separating the fermentation solution withdrawn from the fermenter into a solution containing the bacterial cells and a solution not containing bacterial cells by a cell separator, the solution containing the bacterial cells being circulated from the cell separator to the fermenter by circulating means to perform amino acid fermentation continuously, and bubbles being removed from the fermentation solution by a bubble separator before the fermentation solution is fed to the circulating means and said cell separator.

The apparatus of the present invention for amino acid fermentation comprises a fermenter for retaining at least bacterial cells and a culture medium for amino acid fermentation, a cell separator for separating the fermentation solution withdrawn from the fermenter into a solution containing the bacterial cells and a solution not containing bacterial cells, circulating means for circulating the solution containing the bacterial cells from the cell separator to the fermenter, and a bubble separator provided upstream of the circulating means and the cell separator for removing bubbles from the fermentation solution.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
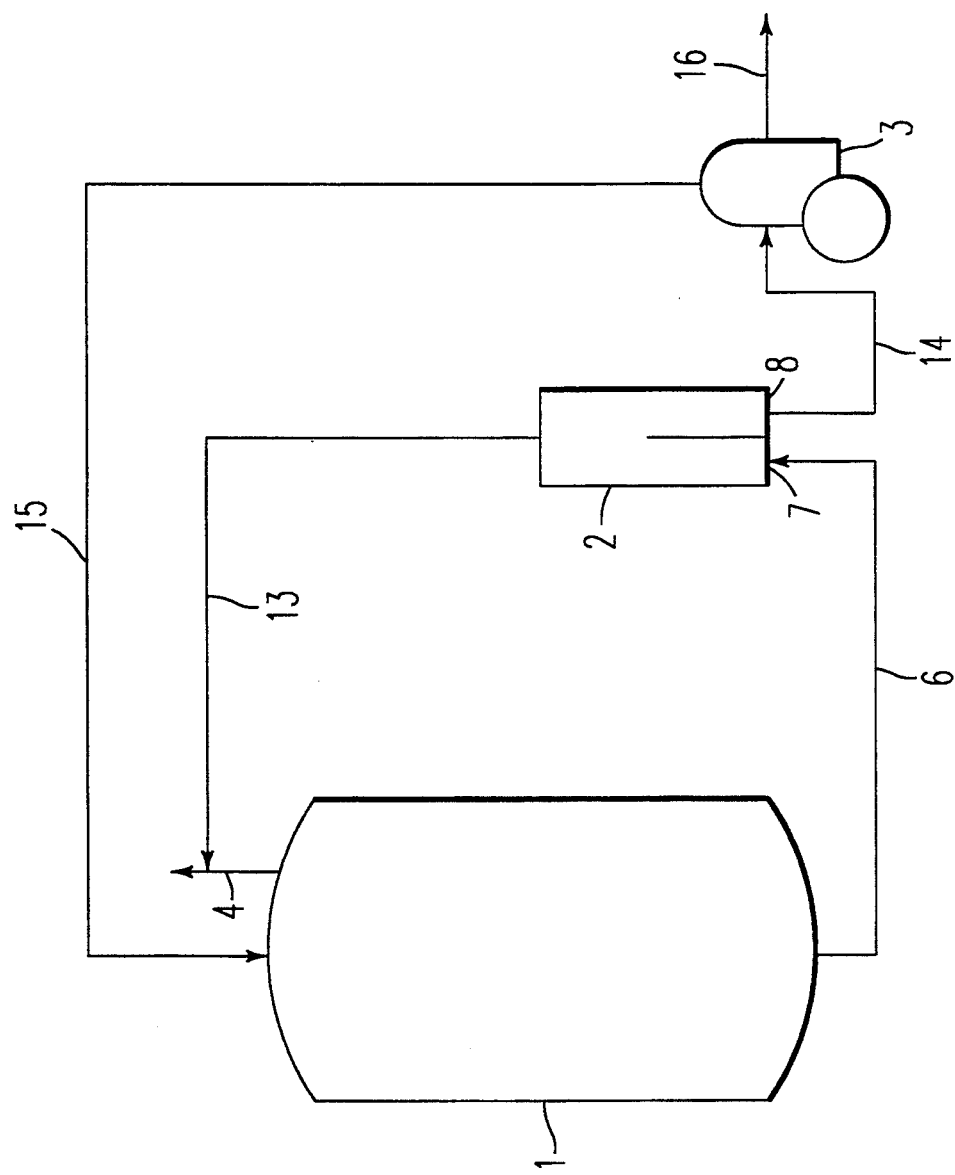
FIG. 1 is a schematic diagram of an apparatus for amino acid fermentation of the present invention.

The bubble separator is provided in the present invention for separating bubbles from the fermentation solution which leaves the fermenter and which contains bubbles. It is, therefore, located upstream of the circulating means and the cell separator. It is preferably situated near the outlet of the fermenter of the fermentation solution to reduce the resistance of the fermentation solution to flow in a pipeline.

The bubble separator may be of any of various types, for example, one which utilizes the tendency of bubbles to rise to the surface of the fermentation solution and allows the gas to pass away into the atmosphere, or one which places the fermentation solution under a reduced pressure.

The fermentation solution leaving the bubble separator should contain nor more than 15%, preferably not more than 10%, of bubbles.

The gas which forms the bubbles which have been separated by the bubble separator may be discharged directly by an exhaust means, or it may be discharged by exhaust means on the fermenter together with the gas which has been generated in the fermenter.

The fermenter, in which amino acid fermentation takes place, has an inlet for bacterial cells and a culture medium and an outlet for the fermentation solution. It is also provided with a temperature control mechanism, a mechanism for the aeration of the fermentation solution, a pH adjusting mechanism, and the like. It may further be provided with an agitating device, and various instruments such as meters for measuring the concentrations of dissolved oxygen, substrate, constituents of the culture medium, and amino acids. It further has a liquid level gauge.

The fermenter may be of any shape such as cylindrical, or box-shaped. It is possible to use any known fermenter.

The cell separator may be of any of various types if it can separate a solution containing bacterial cells from one not containing bacterial cells. It may, for example, be of the type which relies upon filtration, or centrifugal separation. It is, however, necessary to ensure that the bacterial cells not be heated to a high temperature during cell separation. A continuous centrifugal separator can be used as a preferred cell separator for the process of this invention, but if it is of the type which causes the heating of the bacterial cells during separation, it is necessary to cool the fermentation solution before the separation of the bacterial cells.

The circulating means is provided for circulating the fermentation solution containing the bacterial cells between the fermenter and the cell separator, and may, for example, be a propeller pump. The circulating means may be located in a circulating path, or within the cell separator.

The bacterial strain which is used for the purpose of this invention may be any of the strains which are usually employed for amino acid fermentation. If, for example, L-glutamic acid is to be produced, it is possible to use any strain that is usually employed for that purpose, such as *Brevibacterium lactofermentum* ATCC 13869, *Brevibacterium flavum* ATCC 14067, or *Cornyebacterium glutamicum* ATCC 13032.

It is possible to use any known culture medium depending on the amino acid to be produced. If glutamic acid is to be produced, it is possible to use glucose, sucrose, molasses, starch hydrolyzate, ethanol, an organic acid, a hydrocarbon, or any other known substance useful as a carbon source for glutamic acid fermentation.

The culture medium may further contain a source of nitrogen such as ammonium sulfate, ammonium nitrate, ammonium chloride, ammonia, urea, or an amino acid; an inorganic salt such as potassium dihydrogenphosphate, dipotassium hydrogenphosphate, sodium dihydrogenphosphate, magnesium sulfate, or an iron or manganese salt; an organic nutriment such as soybean protein hydrolyzate, biotin or a derivative thereof, a fatty acid or an ester thereof, penicillin or a derivative thereof, and the like. Examples of the fatty acid which it may contain are saturated higher fatty acids having 12 to 18 carbon atom, and examples of the fatty acid ester are glycerol, sorbitan, sucrose and polyethylene glycol esters.

According to the process and apparatus of this invention for amino acid fermentation, the bubble separator separates bubbles from the fermentation solution leaving the fermenter and containing bubbles, so that the solution containing "only a small amount of bubbles" may reach the circulating means and the cell separator, and the circulating means may withdraw and deliver the fermentation solution efficiently without undergoing any cavitation.

In FIG. 1, numeral 1 denotes a fermenter for amino acid fermentation; numeral 2, a bubble separator for separating bubbles from the fermentation solution arriving from the fermenter 1; numeral 3, a cell separator for separating the fermentation solution arriving from the bubble separator 2 after the removal of bubbles into a solution containing bacterial cells and a solution which does not contain bacterial cells.

An exhaust pipe 4 is connected to the top of the fermenter 1, and a pipe 6 to the bottom thereof for receiving and delivering the fermentation solution.

Also connected to the fermenter 1 are a pipe (not shown) for supplying a culture medium and bacterial cells and an air pipe (not shown) for supplying oxygen. A stirring blade (not shown) is provided in the fermenter 1 for agitating the fermentation solution.

Figure 2:
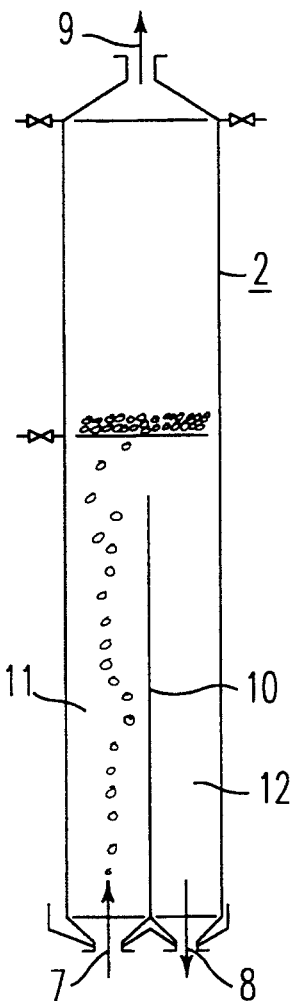
FIG. 2 is a sectional view of the bubble separator of the present apparatus.

The bubble separator 2 is of the upright cylindrical construction, and has an inlet 7 and an outlet 8 for the fermentation solution at its bottom, and an exhaust port 9 at its top, as shown in FIG. 2. A partition 10 extends from the bottom of the bubble separator 2 to its midportion and divides approximately the lower half thereof into an ascending chamber 11 and a descending chamber 12. The inlet 7 is connected to the pipe 6, and an exhaust pipe 13 is connected between the exhaust port 9 and the exhaust pipe 4. The fermenter 1, the pipe 6, the bubble separator 2, and the exhaust pipes 13 and 4 define a circulating path.

The cell separator 3 has an inlet (not shown) through which the fermentation solution arriving from the bubble separator 2, is received, a cell outlet (not shown) through which the solution containing the bacterial cells is discharged, and a solution outlet (not shown) through which the solution not containing bacterial cells is discharged. A pipe 14 is connected between the outlet 8 of the bubble separator 2 for the fermentation solution and the inlet of the cell separator 3. Bacterial cell return pipe 15 is connected between the cell outlet of the cell separator 3 and the top of the fermenter 1. A pipe 16 is connected between the solution outlet of the cell separator 3 and an amino-acid separating and refining apparatus (not shown). Thus, the fermenter 1, the pipe 6, the bubble separator 2, the pipe 14, the cell separator 3 and the bacterial cell return pipe 15 define a circulating path.

The bacterium separator 3 is equipped therein with a pump (not shown) as circulating means for circulating the fermentation solution through the circulating path.

Amino acid fermentation can be carried out by employing the apparatus described above as follows:

A culture medium and bacterial cells are put in the fermenter 1, held at an appropriate temperature, and agitated by the stirring blade to bring about fermentation, while fermenter 1 is supplied with air. The cell separator 3 is placed in operation, and the pump draws the fermentation solution from the fermenter 1 through the pipe 6, the bubble separator 2 and the pipe 14 and returns a part thereof from the cell separator 3 to the fermenter 1.

The fermentation solution is delivered from fermenter 1 to the bubble separator 2 through pipe 6. It enters the ascending chamber 11, rises gradually, and flows over the partition 10 into the descending chamber 12. As it rises in the ascending chamber 11, the bubbles which it contains float to the surface of the solution in the bubble separator 2 and the gas forming the bubbles passes away into the upper vacant space in the bubble separator 2. The gas leaving the bubble separator 2 eventually flows into the exhaust pipe 4 and is discharged with the gas from fermenter 1.

The fermentation solution flowing into the descending chamber 12 is substantially free from any bubbles. It gradually flows down, leaves the bubble separator 2 through the outlet 8, and is delivered to the cell separator 3 through pipe 14. In the cell separator 3, it is separated into a solution containing the bacterial cells and a solution not containing bacterial cells. The solution containing the bacterial cells is returned to the fermenter 1 through the bacterial cell return pipe 15, while the solution not containing bacterial cells is delivered to the amino-acid separating and refining apparatus through the pipe 16.

The bacterial cells which are in the solution which returns from the cell separator 3 to the fermenter 1 also contribute to the amino acid fermentation.

Figure 3:
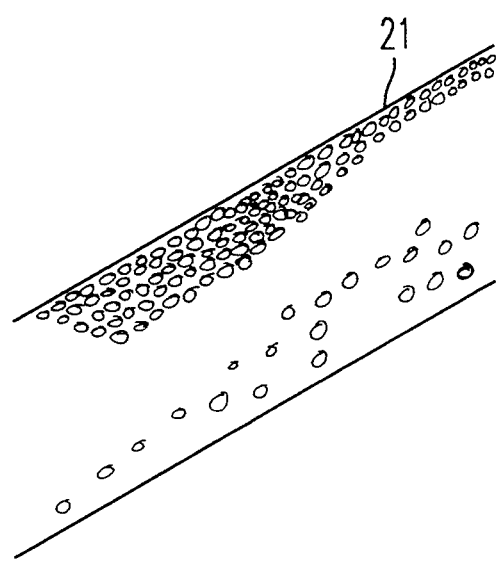
FIG. 3 is a schematic and fragmentary view of another form of bubble separator.

FIG. 3 is a schematic and fragmentary view of another form of bubble separator.

The bubble separator shown in FIG. 3 comprises an inclined cylindrical body 21 having an upper end communicating with the outlet of the fermenter for the fermentation solution. This bubble separator gradually removes bubbles from the fermentation solution, as it flows down from its upper end to its lower end.

Having now generally described this invention, a further understanding can be obtained by reference to certain specific examples which are provided herein for purposes of illustration only and are not intended to be limiting unless otherwise specified.

EXAMPLE 1

Fermenter:
  Total volume: 100 kl (fermenter of the type shown in FIG. 1);
  Internal pressure: 0.5 kg/cm$^2$;
  Aeration rate: 50 m$^3$/min.;
  Charge: 50 m$^3$;
  Stirring blade: Turbine blade;
  Stirring speed: 100 rpm.
Bubble separator:
  Cylindrical residence type bubble separator (of the type shown in FIGS. 1 and 2);
  Residence time of the product of fermentation: about 10 min.
Cell separator and circulating means:
  A centrifugal separator having a pump mounted therein (ALFA-LAVAL,CO.,BTUX-510).
Bacterial strain:
  *Brevibacterium lactofermentum* ATCC 21798.
Culture medium:
Table 1 shows the basic compositions of the seed, main and feed media which were employed.

TABLE 1

| Basic Compositions of Culture Media | | | | |
|---|---|---|---|---|
| Components | Unit | Seed | Main | Feed |
| Sucrose | g/dl | 5.0 | — | — |
| Glucose | g/dl | — | 8.0 | 30 |
| (NH$_4$)$_2$SO$_4$ | g/dl | — | 1.42 | 5.3 |
| KH$_2$PO$_4$ | g/dl | 0.1 | 0.1 | 0.1 |
| MgSO$_4$.7H$_2$O | g/dl | 0.04 | 0.04 | 0.04 |
| FeSO$_4$.7H$_2$O | g/dl | 0.001 | 0.001 | 0.001 |
| MnSO$_4$.7H$_2$O | g/dl | 0.001 | 0.001 | 0.001 |
| Protein hydrolyzate (as total nitrogen) | mg/dl | 150 | 200 | 200 |
| Vitamin B$_1$.HCl | µg/l | 200 | 200 | 200 |
| Biotin | µg/l | 50 | 500 | 500 |
| Nicotineamide | mg/dl | 0.5 | 0.5 | 0.5 |
| Silicone antifoaming agent | mg/dl | 0.005 | 0.005 | 0.005 |

As a result of the working of the invention under the conditions listed above, it was possible to achieve a reduction in the bubble content of the fermentation solution form 30% to 10% and an increase of 1.5 or more times in the solution circulating capacity of the apparatus.

EXAMPLE 2

Fermenter: A Jar fermenter having a total volume of 60 liters;
  Aeration rate: 30 liters/min.;
  Charge: 30 liters;
  Stirring blade: Turbine blade;
  Stirring speed: 600 rpm.
Bubble separator: A cylindrical residence type bubble separator having a total volume of two liters;
  Residence time: About 10 min.;
  Bubble reduction: From 30% to 10%.
Cell separator: A device having a ceramic membrane.
  Circulating means: A liquid pump.
  Bacterial strain: *Brevibacterium lactofermentum* FERM-P 1844.
  Culture medium: Culture media having the compositions shown in Tables 2 and 3 were employed.

TABLE 2

| Seed Medium | |
|---|---|
| Sucrose | 2.0 g/dl |
| Phosphoric acid | 0.1 g/dl |
| MgSO$_4$ | 0.04 g/dl |
| FeSO$_4$ | 0.001 g/dl |
| MnSO$_4$ | 0.001 g/dl |
| Urea | 0.3 g/dl |
| Ammonium acetate | 0.2 g/dl |
| Tyr | 50 mg/dl |
| KOH | 70 mg/dl |
| Protein hydrolyzate (as total hydrogen) | 200 mg/dl |
| Biotin | 100 µg/l |
| Vitamin B$_1$.HCL | 100 µg/l |
| Silicone antifoaming agent | 0.002 mg/dl |

Sterilization: At 120° C. for 20 min.
Seed Culture: At 31.5° C. without pH control.

| Main Medium | |
|---|---|
| Glucose | 23 g/dl |
| MgSO$_4$ | 0.028 g/dl |
| MnSO$_4$ | 0.001 g/dl |
| Phosphoric acid | 0.09 g/dl |
| Biotin | 50 µg/l |
| Vitamin B$_1$.HCl | 2000 µg/l |
| Protein hydrolyzate (as total nitrogen) | 80 mg/dl |

-continued

| Main Medium | |
|---|---|
| Tyrosine | 100 mg/dl |
| KOH | 70 mg/dl |
| Silicone antifoaming agent | 0.002 ml/dl |

As a result of the working of the invention under the conditions listed above, it was possible to achieve the stable circulation of the fermentation solution by the liquid pump at a rate of three liters per hour and the stable production of a solution not containing bacterial cells at a rate of 2.4 liters per hour. The process yielded 0.8 g of phenylalanine per liter per hour and substantially doubled the productivity of the conventional process. When no bubble separator was used, cavitation occurred in the pump and prevented the stable circulation of the solution.

ADVANTAGES OF THE INVENTION

The removal of bubbles from the fermentation solution by a bubble separator installed upstream of the circulating means and the cell separator makes it possible to bring about amino acid fermentation efficiently on a large scale, since no lowering in performance of the circulating means or the cell separator occurs that would otherwise occur.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A process for fermentation to produce an amino acid using fermentation apparatus comprising:
    a fermentor for holding at least bacterial cells in a culture medium and producing an amino acid by fermentation;
    a centrifugal or filtration separator for separating a fermentation solution withdrawn from said fermentor into a solution containing said bacterial cells and a solution not containing bacterial cells;
    a liquid pump for circulating said solution containing said bacterial cells from said centrifugal or filtration separator to said fermentor; and
    a bubble separator provided upstream of said liquid pump and said centrifugal or filtration separator for removing bubbles from said fermentation solution, wherein no pump is present between said fermentor and said bubble separator;
    wherein said process comprises;
    introducing to said fermentor at least bacterial cells in a culture medium;
    fermenting said bacterial cells in a culture medium in said fermentor;
    separating a fermentation solution withdrawn from said fermentor into a solution containing said bacterial cells and a solution not containing bacterial cells, by means of said centrifugal or filtration separator;
    circulating said solution containing said bacterial cells from said centrifugal or filtration separator to said fermentor by means of said liquid pump to perform fermentation continuously to produce an amino acid;
    wherein bubbles are removed from said withdrawn fermentation solution by said bubble separator before said withdrawn fermentation solution is fed to said centrifugal or filtration separator and said liquid pump, wherein the bubble content of a solution leaving said bubble separator is not more than 15%.

2. The process of claim 1, wherein said bubble content is not more than 10%.

3. The process of claim 1, wherein the amino acid produced by fermentation is glutamic acid.

4. The process of claim 1, wherein the bacterial cells fermented are cells of *Brevibacterium lactofermentum* ATCC 13869, *Brevibacterium flavum* ATCC 14067 or *Cornyebacterium glutamicum* ATCC 13032.

* * * * *

UNITED STATES PATENT AND TRADEMARK OFFICE
CERTIFICATE OF CORRECTION

PATENT NO. : 5,362,635
DATED : November 8, 1994
INVENTOR(S) : Toshiki HIROSE, et al.

It is certified that error appears in the above-indentified patent and that said Letters Patent is hereby corrected as shown below:

On the title page, Item [30], the Foreign Application Priority Number is listed incorrectly. It should read:

--2-249983--

Also on the title page, Item [56], the "Attorney, Agent, or Firm" is listed incorrectly. It should read:

--Oblon, Spivak, McClelland, Maier & Neustadt--

Signed and Sealed this

Twenty-eight Day of March, 1995

Attest:

BRUCE LEHMAN

Attesting Officer      Commissioner of Patents and Trademarks